United States Patent [19]

Slater et al.

[11] Patent Number: 5,643,728
[45] Date of Patent: Jul. 1, 1997

[54] METHOD OF MARKING A LIQUID

[76] Inventors: James Howard Slater, 38 Heol-Y-Delyn, Lisvane, Cardiff CF4 5SR, Great Britain; John Edward Minton, 2 Mill Place, Lisvane, Cardiff CF4 5TF, Great Britain

[21] Appl. No.: 392,821

[22] PCT Filed: Aug. 26, 1993

[86] PCT No.: PCT/GB93/01822

§ 371 Date: Feb. 27, 1995

§ 102(e) Date: Feb. 27, 1995

[87] PCT Pub. No.: WO94/04918

PCT Pub. Date: Mar. 3, 1994

[30] Foreign Application Priority Data

Aug. 26, 1992 [GB] United Kingdom ............... 9218131

[51] Int. Cl.$^6$ ............... C07H 21/00; C12Q 1/68
[52] U.S. Cl. ............... 435/6; 435/4; 435/7.1; 435/15; 436/56; 436/57; 436/501; 436/518; 436/526; 436/527; 536/25.3
[58] Field of Search ............... 435/6, 4, 7.1, 15; 436/501, 518, 526, 527, 56, 57; 935/77, 78; 514/44; 536/25.3

[56] References Cited

U.S. PATENT DOCUMENTS

| | | | |
|---|---|---|---|
| 3,736,500 | 5/1973 | Berkowitz et al. | 324/34 |
| 3,853,987 | 12/1974 | Dreyer | 424/1 |
| 3,861,886 | 1/1975 | Meloy | 44/51 |
| 4,264,329 | 4/1981 | Beckett. | |
| 4,359,353 | 11/1982 | Kydd | 149/2 |
| 4,510,244 | 4/1985 | Parks et al. | 431/172.2 |
| 4,552,812 | 11/1985 | Margel et al. | 428/407 |
| 4,672,040 | 6/1987 | Josephson | 436/526 |
| 4,978,625 | 12/1990 | Wagner et al. | 436/518 |
| 5,451,505 | 9/1995 | Dollinger | 435/6 |

FOREIGN PATENT DOCUMENTS

| | | |
|---|---|---|
| 3224484A1 | 1/1983 | Germany. |
| 2017125 | 3/1979 | United Kingdom. |
| WO87/06383 | 10/1987 | WIPO. |
| WO90/14441 | 11/1990 | WIPO. |
| WO91/17265 | 11/1991 | WIPO. |

OTHER PUBLICATIONS

International Search Report; PCT/GB93/01822; 12 Jan. 1994; G. Griffith.

*Primary Examiner*—Stephanie W. Zitomer
*Assistant Examiner*—Paul B. Tran
*Attorney, Agent, or Firm*—Fish & Richardson P.C.

[57] ABSTRACT

A method of marking a liquid and subsequently detecting that the liquid has been marked, which method comprises: adding to the liquid an additive comprising a plurality of particles in an amount no greater than 1 part weight of particles per $10^6$ parts weight liquid, the particles comprising signal means to aid their detection and not being visible in the liquid to the naked eye; sampling a portion of the liquid containing said additive, and detecting the presence of particles in the liquid, with the proviso that said signal means does not consist solely of a nucleic acid tag.

24 Claims, No Drawings

METHOD OF MARKING A LIQUID

CROSS-REFERENCE TO RELATED APPLICATIONS

This application corresponds to PCT/GB93/01822 filed on Aug. 26, 1993. The latter application is a continuation application claiming priority, in turn, from GB Serial Number 9218131.2 filed on Aug. 26, 1992.

BACKGROUND OF THE INVENTION

This invention relates to the marking of materials and in particular to a method of marking a liquid and subsequently detecting that the liquid has been marked.

There is a widespread requirement to be able to trace the path taken by a given material as it moves from one location to another. In general terms, two broad categories of material movement are recognised:

(i) The movement of materials as a result of natural processes occurring in the biosphere, e.g., the flow of water in sub-surface aquifers, the movement of sediments etc.

(ii) The movement of materials which have been manufactured by man, i.e., items which do not occur in the natural environment or which are natural materials being transported as a result of man's activities. The former would include any item produced by man, and the latter items such as grain and other food materials, mineral ores and petroleum products, such as crude oil.

In all these situations, there may be reasons why it is necessary to develop specific procedures to trace these movements. It may be that direct observation is not possible, e.g., when following the path of an underground stream. It may be that it is necessary to monitor the movement of goods without the direct knowledge of the transporters or, for legal reasons, to prove that the appearance of a material at a particular point in the biosphere was due to the same material originating from a known starting point.

For example, it is undesirable and in certain circumstances illegal, for petroleum materials to leak from storage sites or transportation containers and contaminate the natural environment. Petrol storage tanks, e.g., at petrol filling stations, are usually located underground. Should one of these tanks develop a leak, the loss of material will eventually be detected, either by audits on the material being added to and removed from the storage tank, or by detection of spilt, leakage material at some site adjacent the storage tank area. Since the tanks are underground, visual inspection is not normally possible and it is a costly procedure to excavate successive tanks to determine which tank is the cause of the leakage. The normal procedure would be to develop a protocol whereby a known marker, e.g., a dye, is added to the tanks to determine, by tracing the movement of the dye, which tank is the cause of the leakage. Cheaper remedial action can then be taken to deal with the identified leaking tank. One feature of this procedure is that, in order to know which tank is leaking, the markers added to each tank must be different, i.e., if there are six tanks, then six different dyes, each recognisable by some property which can be accurately and uniquely determined, need to be used. The greater the number of individual components in a particular system, the greater the number of unique traces that need to be used to make the necessary distinction between the paths taken by different leaks from different tanks.

Another example concerns the identification of the source of pollution in the sea and waterways from spills of petroleum materials, particularly oil. The environmental damage caused by accidental oil spills and deliberate dumping of oil by ships, e.g., when washing tanks, is significant and there is a growing demand for the culprits to be identified and to be held responsible for clean-up operations. One of the problems associated with the identification of oil samples in large volumes of aqueous media, such as an oil slick on the sea, is that any marker introduced into oil has a tendency to partition out or be dispersed in the aqueous phase, rendering collection and identification of the marker particularly difficult.

A further example illustrating the need to monitor the movement of a liquid from one location to another is provided by the practice of adding to fuel oils, additives, such as antistatic agents, detergents etc., in order to improve the performance of the oil. It is important that persons dealing in such materials are aware whether they have been treated, but many of these additives are only added in amounts which cannot be detected without recourse to complex and often expensive analytical procedures, and in certain instances it is not readily possible to determine whether the additive has been added at all, because its presence is effectively masked by impurities in the fuel oil. For example, antistatic agents often incorporate chromium ions whose detection is relatively straightforward. However, naturally occurring levels of chromium in oil are often far in excess of that introduced by the antistatic agent. It has been proposed to dye the oil to indicate the presence of these additives, but the amount of dye which must be added to produce a visible colour change in such materials is unacceptable to both producer and consumer alike, e.g., for reasons of cost, possible loss of performance, potential damage to engines etc and the amount may exceed threshold limits set by standards.

Another example is provided by the exemption from value-added-tax (VAT) of fuel oils for agricultural machinery and seagoing vessels. It has been known for unscrupulous individuals to take advantage of this exemption, by using such fuel for purposes for which there is no exemption, such as motor cars, thereby depriving the government of revenue.

In addition, there are many reasons why individuals, corporations, public bodies and governments might wish to mark materials, e.g., to monitor the flow of materials along distribution and sales networks, in order to be able to determine the ultimate fate of that material and/or the efficiency of a particular distribution network compared with another.

Many tracing methods have been used to solve problems of this sort, all of which involve the addition of some characteristic marker, such as dyes or radioactive compounds, to the material being monitored. Biological materials, such as bacteriophage or bacteria have also been used, most notably for tracing the movement of water bodies in the natural environment. In these cases, the living systems possess some property (e.g., a known drug resistance pattern or particular host specificity) which does not normally occur in nature. The added organisms can be traced from their point of addition by obtaining samples as required, isolating any organisms in those samples, and showing that the organisms originally added can be isolated from the samples.

International Patent Publication No. WO 87/06383 discloses a method of labelling an item or substance which involves labelling with a macromolecule, such as nucleic acid or a polypeptide. The method takes advantage of the ability to detect the presence or absence of molecules, such as DNA or protein per se, by simple chemical analytical procedures, referred to as "YES/NO" tests, which indicate whether or not the macromolecule is present. For example, the presence of DNA can be detected by using non-specific chemical agents which bind to the DNA, such as ethidium bromide, acridine orange or bis-benzimide (H33258, Heochst dye 33258). In the case of ethidium bromide, this compound cannot be detected under normal visual light wavelengths. Labelling may therefore be achieved by providing DNA and ethidium bromide together. The presence of the DNA (with bound ethidium bromide) can subsequently be detected by ultraviolet irradiation. There is no discrimination between different DNA molecules from different sources, e.g., from different organisms.

The resolution of the system may, however, be considerably improved by taking advantage of the ability of macromolecules, such as nucleic acids and proteins, to be recognised unequivocally by a second complementary macromolecule to provide a unique marker. Accordingly, it is possible to determine the authenticity of an item or substance, by labelling that item or substance with a predetermined macromolecular first compound capable of binding to a second complementary macromolecular compound and using that second compound as a probe to determine the presence or absence of the first compound and thus establish whether a given item or substance is the genuine (marked) article.

The uniqueness of DNA to each species and, indeed, each strain within a species, together with the technical capacity to hybridise unique DNA molecules provides a more sophisticated form of labelling than a simple "YES/NO" test. For each strain of organism, the DNA (or RNA) molecules are unique, although different strains of the same species differ by virtue of small variations in sequences of bases. It is possible to recognise the DNA of different species and different strains of the same species by examining the DNA with labelled DNA probes. An item or substance may be labelled with a "signal DNA" comprising a sequence capable of hybridising with a specific "probe DNA". Both the signal DNA and the probe DNA are kept secret. Where analysis of the labelled item or substance by means of the probe DNA reveals the signal DNA, the item or substance is genuine. If not, the item or substance is an imitation.

This marking technique is primarily intended for labelling articles, such as luxury goods, e.g., watches, perfume and clothes; films and recordings; bank notes; art works; documents such as passports, and machinery and parts, e.g., for cars, although reference is made to labelling pharmaceuticals and other chemicals, such as fertilisers, herbicides and pesticides.

Labelling may be achieved in a variety of ways, e.g., the signal compound may be incorporated directly into the item or substance during its manufacture, or it may be attached by an adhesive. The signal compound may also be included in a material such as a paint or ink which is applied to an item or substance.

International Patent Publication No. WO 90/14441 discloses a method of monitoring the presence of a substance which comprises marking the substance with a nucleic acid tag, collecting the substance and detecting the tag, generally by amplifying the nucleic acid using polymerase chain reaction technology. The polymerase chain reaction (PCR) procedure is disclosed in, e.g., U.S. Pat. Nos. 4,683,202 and 4,683,195, and European Patent Publication Nos. 258017 and 237362, and allows for the enzymatic amplification, in vitro, of specific DNA sequences using oligonucleotide primers which recognise all or part of the DNA molecule used as the taggant. The use of PCR technology enables the DNA molecule to be amplified exponentially, e.g., 25 complete cycles of amplification enables a single DNA molecule to be increased $3.4 \times 10^7$ times.

Also disclosed is a kit designed to tag and monitor substances comprising a nucleic acid taggant and a polynucleotide complementary to the taggant which can be either a signal probe, capture probe or a primer for the PCR method. Reference is made to the kits containing "signal means", such as enzymes, radio-isotopes and fluorescent labels, but no further details are provided.

Substances which may be tagged are said to include air pollutants, organic solvents (such as those from dry cleaners, chemical factories, airports and petrol filling stations), explosive compositions (such as plastic explosives and gunpowder), paper goods (such as newsprint, money and legal documents), pharmaceutical products (such as medicaments), inks, perfumes and paint products.

The nucleic acid may be free, i.e., naked, encapsulated by polymeric substances (such as proteins) or lipophilic compositions (such as liposomes), bound to a component of the tagged substance or bound to a solid support which is then mixed with the substance being tagged. Suitable support materials are said to include latex, dextran and magnetic beads, but no further details are provided.

Our copending International Patent Publication No. WO91/7265 also discloses a method for tracing the origin and movement of materials, both liquid and solid, which comprises: adding to the material a microtrace additive comprising DNA molecules; sampling the resulting material after movement thereof, and detecting the presence of the microtrace additive in the sample.

In a preferred aspect of the invention, the material being monitored is a liquid hydrocarbon, such as oil, and the microtrace additive is designed such that it cannot be easily removed from the hydrocarbon by aqueous washing, e.g., following an oil spill at sea. In mixtures of water and hydrocarbons, any DNA present in the hydrocarbon tends to move to the aqueous phase. The partitioning of DNA under these conditions is due to the negative charges associated with the phosphodiester groups of the DNA and the ability to form hydrogen bonds with water molecules and an inability to do so in a hydrocarbon environment. Various methods are proposed for ensuring that the DNA remains in the hydrocarbon rather than partitioning to any aqueous phase, including covalently linking the DNA to hydrophobic beads, typically of from 1 to 5 μm diameter, designed to be soluble in hydrocarbons and not the aqueous phase.

By taking advantage of recent advances in techniques, such as PCR technology, for the detection of DNA at exceedingly low concentrations, only small quantities of DNA, typically in the concentration range $1 \times 10^{-11}$ to $1 \times 10^{-6}$ g DNA per ml of oil or other liquid, are used in the microtrace additive. For example, plasmid pBR322 DNA ($2 \times 10^{-9}$ g), chosen because DNA primers for amplification of this molecule are commercially available, was added to Arabian light crude oil (100 μl) and mixed. To subsequently extract the DNA, distilled water (100 μl) was added to the oil and the mixture thoroughly mixed to extract the pBR322 DNA from the oil into the aqueous phase. The oil-water mixture was centrifuged (10000 xg for 5 minutes) and the aqueous phase layer (5 μl) removed and loaded into a standard Taq polymerase PCR reaction vial and reaction mixture (100 μl containing KCl (50 mM); Tris-HCl buffer (10 mM; pH8.4); MgCl$_2$ (1.5 mM); gelatin (100 µg/ml); two pBR322 DNA primers (0.25 µm); deoxyribose nucleotide phosphates (200 µg of each of dATP, dCTP, dGTP, dTTP), and Tag polymerase (2.5 units). Following automated PCR cycling, the reaction mixture (10 µl) was loaded onto agarose gel (2% w/v) and electrophoresed under standard conditions. The completed gel was stained with ethidium bromide to visualise the amplified DNA. No bands appeared in various negative controls.

Whilst DNA is particularly suitable for use as a unique marker, there are many instances where all that is required is a simple "YES/NO" test of the type described previously, e.g., to indicate that a particular fuel oil has been treated with a certain additive etc. In such circumstances, DNA is a less effective marker, as the DNA must either be present in prohibitively large amounts for it to be detected by non-specific assays, such as ethidium bromide staining, or PCR techniques are required to increase the amount of DNA to a level which can be detected. Thus, there is a continuing need for an accurate, reliable and cost-effective method of marking a liquid which is capable of providing a "YES/NO" test, and which does not rely on the use of complex, time-consuming analytical procedures or the use of unacceptably high levels of marker.

Many of the immunodiagnostic assays performed in clinical laboratories utilise a bioreactive molecule, typically an antibody, having a specific binding affinity for a target molecule, e.g., the antigen in respect of which the antibody was raised, in order to identify and/or isolate that target molecule in a given test sample. The bioreactive molecule is often coupled to the surface of a microbead, in order to increase the total surface area available to capture the target molecule and to facilitate the separation of bound target molecules from a solution of free molecules, since they can easily be immobilized, e.g., on a filter. Such beads are typically formed of a polymeric material, and generally have a diameter within the range from 0.05 to 100 µm. The beads may be provided with a label, such as a fluorescent label, radiolabel etc., to provide signal means. Other beads are magnetic to aid their separation from the test sample, e.g., a magnet can be used to pull the beads into one region of the test vessel from which they can be physically separated. Magnetic beads can be prepared by dispersing particles of a magnetic material, such as magnetite (Fe$_3$O$_4$), into the polymeric material used to form the particles.

Such microbeads are widely used in several fields of biochemistry and medicine, including the isolation of cells and target molecules from whole blood, tissue extracts, tissue cultures, enzyme digests and solid tissues; tissue typing; the isolation of PCR or Klenow DNA fragments; as carriers for pharmaceutical preparations; the separation of cancer cells from healthy cells; to provide a ready prepared template for genome walking, and the selective enrichment and/or isolation of pure and viable micro-organisms or smaller target compounds like soluble antigens, e.g., as disclosed in British Patent Publication No. 2017125, U.S. Pat. Nos. 4,035,316, 4,105,589, 4,138,383, 4,186,120, 4,224,198, 4,259,223, 4,267,237, 4,326,008, 4,369,226, 4,410,370, 4,510,244, 4,530,956, 4,550,017, 4,552,812, 4,563,510, 4,622,362, 4,654,267, 4,654,300, 4,663,277, 4,678,814, 4,689,307, 4,783,336, 4,828,984, 4,962,023, 5,028,545, and 5,081,020, and European Patent Publication Nos. 91453, 10986 and 106873.

Microbeads bearing fluorescent labels are commonly used to align, calibrate and correct apparatus, such as fluorescence microscopes and flow cytometers, e.g., as disclosed in U.S. Pat. Nos. 4,224,359, 4,714,682, 4,774,189, 4,857,451, 4,868,126, 4,918,004, 5,073,497, 5,084,394 and 5,093,234.

SUMMARY OF THE INVENTION

The present invention seeks to provide an alternative method for the marking of liquids.

According to one aspect of the invention there is provided a method of marking a liquid and subsequently detecting that the liquid has been marked, which method comprises:

adding to the liquid an additive comprising a plurality of particles in an amount no greater than 1 part by weight of particles per $10^6$ parts weight liquid, the particles comprising signal means to aid their detection and not being visible in the liquid to the naked eye;

sampling a portion of the liquid containing said additive, and detecting the presence of particles in the sample, with the proviso that said signal means does not consist solely of a nucleic acid tag.

In the context of the present invention, any reference to the particles "not being visible in the liquid to the naked eye" is to the individual particles, when dispersed in the liquid, not being visible without recourse to optical aids, such as microscopes.

The term "liquid" should be construed sufficiently broadly to encompass viscous and semisolid materials, such as tars, bitumen resins, paint products, syrups etc. It should also be construed as encompassing liquid materials which are subsequently stored, transported or used in solid or semi-solid form, e.g., inks, paint products etc.

The samples need not be drawn from the main body of the liquid, but from the environment, e.g., the sea in the case of an oil spill, nor do the samples have to be in the form of a liquid, e.g., where a waste material has been illegally discharged into the soil, samples of earth may be recovered, even after a period of time has expired, and analyzed.

The term "hydrocarbon" is to be construed broadly as relating to any organic compound having as a major component thereof carbon and hydrogen, thereby encompassing not only compounds consisting solely of carbon and hydrogen, including both aliphatic and aromatic and saturated and unsaturated compounds, but also compounds containing heteroatoms, such as oxygen, nitrogen, sulphur, selenium, vanadium etc., e.g., alcohols, ethers and the like.

The term "oil" should be construed as describing any water-insoluble, liquid, including those derived from petroleum, coal, shale etc., by distillation, cracking and chemical treatment, and fixed (or fatty) oils obtained from animals and plants, such as olive oil, palm oil, rapeseed oil, sunflower oil, whale oil etc.

The method of the invention provides an accurate, reliable and cost-effective method of marking a liquid, which may be used as a simple "YES/NO" test or, if desired, as a more specific test for tracing the origin and/or movement, from one location to another, of liquids. The method can be used to mark substantially any liquid, although for most purposes it use will be confined to more valuable liquids, such as crude oil, fuel oils, e.g., petrol, diesel oil, paraffin, aviation fuel etc. In addition to hydrocarbons, the present invention finds utility in the marking of liquids as diverse as perfumes, inks, paint products, pharmaceuticals and other chemicals, such as fertilisers, herbicides, pesticides and organic solvents, waste discharges from factories, refineries, power stations, nuclear waste etc.

According to a further aspect of the invention there is provided a liquid containing an additive comprising a plurality of particles added in an amount no greater than 1 part by weight of particles per $10^6$ parts weight liquid, the particles comprising signal means to aid their detection and not being visible in the liquid to the naked eye, with the proviso that where said signal means comprises a nucleic acid tag, either the particles further comprise a second different signal means or said additive also comprises particles having signal means comprising other than a nucleic acid tag.

DETAILED DESCRIPTION OF THE INVENTION

The choice of particles for use as the additive is primarily dependent on the type of liquid being marked. For example, different considerations arise when marking crude oil when compared with perfume, both in terms of the nature of each material, e.g., viscosity (specific gravity), hydrophobicity, opacity etc., the manner in which the material is treated, stored and transported and the purpose to which the material will be put. Obviously, there are far less restrictions on what can be added to a shipment of crude oil for refining than to a perfume, and the logistics of marking a 250,000 tonne shipment of crude oil are very different from those for marking 250 ml bottles of perfume. For example, in the former case, it is important that the particles are evenly dispersed throughout the entire cargo if it is to be used to trace the guilty party in the event of an oil spillage, whereas in the latter case, the bottle of perfume need only be shaken prior to sampling when testing, e.g., the wares of a street trader suspected of peddling stolen goods.

The density of the particles is advantageously matched with the specific gravity of the liquid being marked to ensure that the additive will, once added to the liquid, remain evenly distributed throughout the liquid. However, in relation to oil carried by tankers, settling will be counteracted to some extend by pumping and slopping of the cargo. Even distribution is an important consideration where, e.g., it is intended to discourage illegal activities, such as black marketeering, the washing of oil tanks at sea etc., or where the liquid is subsequently to be divided into smaller volumes.

The particles should be compatible with the liquid, e.g., when marking oils and other hydrophobic materials, the particles should be of hydrophobic (lipophilic) character to minimise the possibility of their partitioning into the sea in the event of a spillage. The particles advantageously do not dissolve in the liquid, but form a very fine dispersion to allow their subsequent separation from the liquid.

The particles may have any size or shape appropriate for the intended purpose, e.g., they may be solid or hollow, of regular or irregular shape etc., although for most purposes they preferably constitute a homogeneous population of substantially identical size, shape, density etc., such that the behaviour of the particles in the liquid can be predicted.

The particles are added to the liquid in an amount no greater than 1 part by weight particles per $10^6$ parts weight liquid, although it will be appreciated that it is sometimes necessary to add the particles in greater amounts, e.g., in the case of a concentrate, in anticipation of subsequent dilution. The particles are preferably added in an amount no greater than 1 part by weight per $10^8$ parts weight liquid, more preferably in an amount no greater than 1 part by weight particles per $10^{10}$ parts weight liquid. The particles are typically added to the liquid in an amount of from about 1 part by weight particles per $10^{10}$ parts weight liquid to about 1 part by weight particles per $10^{12}$ parts by weight liquid.

The particles may be formed of any suitable non-living or non-viable formerly living matter material, including (but not limited to): polymeric materials (whether synthetic or naturally occurring), ceramic materials, glasses and the like, with the general proviso that the particles are inert, i.e., non-reactive, to the liquid being marked. Polymeric materials are preferred and examples of suitable polymeric materials include (but are not limited to): polyether sulphones; polyimides, such as polyimide-amides and polyether imides; polysulphones; cellulose esters, such as ethyl cellulose, cellulose acetate, celulose acetate hydrogen phthalate, cellulose acetate butyrate, cellulose acetate propionate, cellulose triacetate etc.; polyvinyl resins, such as poly(vinyl acetate), poly(vinyl chloride), poly(vinyl pyridine), poly(vinyl alcohol) etc.; polyacetals, such as poly(vinyl butyral), poly(vinyl formal) etc.; polyesters, such as poly(ethylene terephthalate), poly(ethylene naphthalate) etc.; fluorinated polymers, such as poly(vinylidene fluoride), poly(tetrafluoroethylene), poly(tetrafluoroethylene-hexafluoropropylene) etc.; polyacrylates, such as polyacrylic acid, polymethacrylic acid, polymethylmethacrylic acid etc; latex and other rubbers or gums; polycarbonates; polyolefins, such as polyethylene, polypropylene, polystyrene etc; polyamides, such as nylon, and dextran, starch and other polysaccharides.

In a preferred embodiment of the invention, the particles comprise microbeads or microspheres. Exemplary microbeads/spheres are commercially available from Dynal (U.K.) Ltd. of Wirral, Merseyside, U.K., under the generic tradenames DYNABEADS and DYNASPHERES. The preparation of these beads is disclosed in, e.g., European Patent Publication Nos. 91453, 10986 and 106873 and U.S. Pat. Nos. 4,186,120, 4,530,956, 4,563,510 and 4,654,267.

The particles are preferably present such that there are on average not more than 1000 particles per ml of liquid, more preferably not more than 100 particles per ml of liquid and most preferably between 1 and 100 particles (inclusive) per ml of liquid, with a typical amount about 10 particles per ml.

The particles may have any size suitable for the intended purpose, with the proviso that individual particles should not be visible (in the liquid) to the naked eye. Generally, particles having an average size not greater than about 5 µm are suitable for most purposes. The particles preferably have an average size of from 0.01 to 5 µm, more preferably 0.05 to 1 µm, with a typical size about 0.25 or 0.5 µm.

The particles may advantageously be of such a size that they exhibit Brownian motion in the liquid. This phenomenon may be used to aid the formation of a substantially uniform distribution of particles throughout the liquid.

The signal means to aid the detection of the particles in the liquid may take a wide variety of forms, but is preferably of the type that will allow the person testing the liquid to determine the presence or absence of the particles relatively quickly, preferably within a few minutes and certainly within a few hours. The detection procedure preferably does not involve the use of complex analytical procedures and techniques, although some experimental manipulation is inevitable. The testing procedure is preferably such that it can be conducted on site, i.e., on board a marine tanker, at the site of a storage tank etc., without sending samples to a laboratory.

The following recitation is provided by way of example only and should not be considered to be exhaustive:

(1) The particles may be magnetic. A sample of liquid suspected of containing magnetic particles can be analyzed, e.g., by using a magnetic probe to extract the particles from the liquid. The isolated particles can then be further analyzed. Alternatively, a magnet can be used to pull the beads into one region of the test vessel from which they can physically separated. Suitable magnetic beads are commercially available from Dynal (U.K.) Ltd. of Wirral, Merseyside, U.K., under the generic trade name DETACHaBEAD, and are disclosed in, e.g., U.S. Pat. No. 4,654,267. Apparatus for the separation of magnetic microspheres is likewise available from Dynal (U.K.) Ltd., under the trade names MCP-1, MCP-6 and MCP-E.

(2) The particles may have a known size or shape distribution to allow a particular batch to be identified, by determining the frequency of particles of one size or shape relative to the other. Particle size (volume) can be determined by the Coulter principle based on the change in electrical impedance due to each particle, and can be used to distinguish particles of identical or overlapping size ranges, provided the particles have different impedance characteristics. Labels providing significant differences in electrical impedance, e.g., metal particles, such as gold, may be used to provide such a signal. Thus, particle-based assays can be performed using a Coulter counter without having to separate the particles prior to testing.

(3) The particles may be coloured, e.g., by dispersing appropriate pigments into the beads during their preparation, although this is generally only practical for larger particles. The additive may comprise particles of a single colour or a number of colours, with the distribution of the differently coloured particles selected to allow a particular batch to be identified, by determining the frequency of the different coloured beads in given sample.

In a preferred aspect of the invention, the particles are used to concentrate, in the region of the particle, what would otherwise be very low amounts of a signal label, i.e., amounts which, if uniformly dispersed throughout the liquid, would produce a concentration of label too low to be readily detected. This aspect of the invention will now be described with reference to (4) to (6) below.

(4) The particles may be provided with a fluorescent, luminescent or phosphorescent label. "Fluorescence" describes the emission of light of a different (usually greater) wavelength by a substance following exposure to exciting radiation. "Luminescense" describes the emission of light under the influence of various physical agents, e.g., chemical agents (chemiluminescence) etc. "Phosphorescence" describes the emission, usually after a defined interval, of light by a substance following exposure to heat, light or electric discharge. It will be appreciated that these terms are not mutually exclusive and there is some overlap between such labels.

The preferred signal means for use in the method of the invention are fluorescent substances, especially fluorescent dyes, e.g., of the type commonly used in fluorometric flow cytometry. Suitable fluorescent dyes include (but are not limited to): allophycocyanine, phycocyanine, phycoerythrine, rhodamine, oxazine, coumarin, fluoroscein derivatives, e.g., fluorescein isothiocyanate and carboxyfluoroscein diacetate, as well as Texas red, acridine yellow/orange, ethidium bromide, propidium iodide, bis-benzamide (commerciallly available from Hoechst under the trade name H33258) etc. A sample of liquid suspected of containing particles bearing a fluorescent label may be easily and rapidly analyzed using, e.g., a fluorescence microscope or a flow cytometer.

The additive may contain two (or more) types of particles, each type bearing a differently coloured label. Qualitative differences in the signals from the labels, e.g., fluorescence wavelength, will distinguish the respective particle populations. The distribution of the particle types may be selected such that it is possible, by examining the frequency of each label in a given sample, to identify a particular batch of liquid.

Particles capable of emitting light following irradiation by exciting radiation can be amplified using, e.g., a photomultiplier. This technique is especially useful if the light emitted by the particles is of a different wavelength to the exciting radiation, as is the case with phosphorescent labels. A laser may be used as the irradiating source. Alternatively, polarised light may be used.

Conventional flow cytometers use light scattering to detect each particle and, as the light scattering signal is proportional to particle size, particles of different sizes can also be distinguished, providing the size-ranges of the respective populations do not overlap. In general, the concentration of particles in an unknown sample can be determined by measuring, the fluorescence intensity of the particles and reading the corresponding concentration from a standard curve (where particle concentration is a function of fluorescence intensity). The particles of each population are preferably uniform in size as well as surface area characteristics, since this results in less variance in fluorescence per particle. The aforedescribed DYNOBEADS and DYNOSPHERES are perfect spheres with a relative standard deviation (CV) in light scatter measurements of about 1%. A number of such particle types can therefore be mixed and still easily identified as non-overlapping populations in a flow cytometric light scatter histogram. Thus, reading of particle-based assays can be performed by flow cytometry without having to separate the particles prior to reading.

Other labels providing a photometric signal, including colloidal gold particles etc., may also be used.

(5) An enzyme may linked to the particles. Suitable enzymes and assay procedures are well known, but useful examples include (but are not limited to): alkaline phosphatase or other transferase, catalase, β-galactosidase, horseradish peroxidase and luciferase. A sample of liquid suspected of containing particles bearing an enzyme can be analysed by addition of that sample or, if the liquid, e.g., oil, does not allow direct addition of the sample, as most enzyme reactions are aqueous based, the isolated particles, to a reaction mixture containing the appropriate substrate and such enzyme cofactors as are necessary, and monitoring the reaction catalysed by the enzyme, e.g., by the appearance of a reaction product or the removal of the enzyme substrate.

For example, referring to the above exemplified enzymes, luciferase can be detected by the emission of light caused by the breakdown of ATP to ADP+P.

β-galactosidase can be detected spectrophotometrically using "X-gal" [5-bromo-4-chloro-3-indolyl-β-D-galactoside] which is a colourless, chromogenic substrate cleaved by β-galactosidase to release a blue indolyl derivative. The use of β-galactosidase and X-gal is well known in bacteriology.

Any enzyme, such as alcohol oxidase, aldehyde oxidase, amino-acid oxidase, ascorbate oxidase, galactose oxidase, glycollate oxidase, glucose oxidase, hexose oxidase, lactate oxidase, malate oxidase, NADH oxidase, oxalate oxidase, pyruvate oxidase, tryptophan oxidase, urate oxidase and xanthine oxidase which, directly or indirectly, consumes or requires oxygen, can be monitored by measuring the rate of oxygen uptake or evolution. For example, glucose oxidase catalyzes the consumption of oxygen according to the amount of glucose available, as expressed by the equation:

$$C_6H_{12}O_6 \cdot H_2O + O_2 \rightarrow C_6H_{12}O_7 + H_2O_2$$

The resulting decrease in oxygen can be sensed by an oxygen electrode. Redox dyes directly coupled or indirectly coupled through an enzyme-glucose reaction could also be used to provide a colorimetric change.

The enzyme may produce hydrogen peroxide as a by-product which can be sensed by a hydrogen peroxide sensitive electrode, e.g., a $H_2O_2$ polarographic anode. A colorimetric method may be used for detecting amounts of hydrogen peroxide produced by the enzyme reaction, e.g., the amount of hydrogen peroxide produced may be measured by a system which comprises a chromogenic reagent or reagents capable of undergoing a colour change in the presence of hydrogen peroxide. One known method of such measurement is by means of a quadravalent-titanium and xylenol orange which react to form a stable red colour with hydrogen peroxide (Taurenes & Nordschow, *American Journal of Clinical Pathology*, Vol. 49, p. 613, 1968). The amount of hydrogen peroxide produced is measured by the intensity of the colour. Alternatively, an enzyme such as catalase which reacts with hydrogen peroxide according to the following reaction scheme:

$$2H_2O_2 \rightarrow 2H_2O + O_2$$

can be monitored by measuring the amount of oxygen evolved or the removal of the hydrogen peroxide.

The reaction may also be followed by measuring the electrons which are removed during the enzyme reaction and transferred to a coloured dye, e.g., lactic acid dehydrogenase removes electrons from lactic acid which are then available for transfer to a coloured dye. Alternatively, electrons removed during the enzyme reaction may be transferred directly to an appropriate "biosensor" which generates an electronic signal proportional to enzyme activity. Suitable biosensors are well known in the field of biochemistry and provide a much simpler way of quantifying enzyme activity when compared with colorimetric methods.

A $pCO_2$ electrode may be used to measure the carbon dioxide evolved from the action of decarboxylases, such as acetoacetate decarboxylase, arginine decarboxylase, aspartate decarboxylase, glutamate decarboxylase, lysine decarboxylase and pyruvate decarboxylase.

(6) The signal means may comprise a radiolabel. A sample of a liquid suspected of containing particles bearing a radiolabel can be analyzed using a Geiger-Müller tube or scintillation counter, or by coating a thin film of the liquid onto an appropriate substrate and overlaying it with a photographic film, the radiolabel causing fogging of the film in those regions immediately adjacent the particles. The radiolabel must be added in amounts greater than the naturally occurring radioactivity of the liquid. Suitable radiolabels are well known in the field of biochemistry, e.g., $^{32}P$, $^{35}S$ and $^{125}I$.

The attachment of radiolabels, enzymes and the like to particles, is well known in the context of immunodiagnostic kits etc., and will not be described herein.

The particles may have to be removed from the liquid prior to any testing, depending on the nature of the liquid and the type of signal means used. This is especially true of enzymatic labels which are usually aqueous based. Separation of the particles may be accomplished by a wide variety of techniques, e.g., centrifugation, filtration, the use of a magnet to separate magnetic particles, column chromatography etc. Alternatively, the particles may be coated with a molecule having a strong binding affinity for another molecule. The particles may be removed or concentrated by passage through a column comprising that other molecule bound to a solid support matrix or the sample may be washed over a substrate, e.g., a microscope slide, to which that other molecule has been anchored. Suitable pairs of binding molecules include (but are not limited to): antigen and specific antibody; hormone and hormone receptor; hapten and antihapten; polynucleotide and complementary nucleotide; polynucleotide and polynucleotide binding protein; biotin and either of avidin and streptavidin, especially streptavidin; enzyme and enzyme cofactor, and lectin and specific carbohydrate.

The use of streptavidin and biotin is especially preferred, as streptavidin has a very high binding constant (almost irreversible). Particles bearing one of avidin/streptavidin and biotin may be concentrated by a procedure, such as column chromatography, thereby enabling more dilute dispersions of the additive to be used, or simpler methods for the detection of the appropriate label carried by the particles.

(7) These surface bound molecules can also be used as a means to aid detection of the particles in their own right. For example, using techniques similar to those employed in indirect (or sandwich) immunoassays, a reagent containing one of each pair of specific binding molecules bearing a label, e.g., an enzyme, fluorolabel, radiolabel etc., may be added to the sample suspected of containing particles. Any particles present are then isolated and washed to remove unbound reagent and the presence of the label detected as described previously. Alternatively, a probe coated with one of a pair of specific binding molecules can be used to extract particles coated with the complementary molecule from the liquid. If necessary, the probe and beads can be examined under a microscope.

(8) The additive may comprise two (or more) different types of particles, each having a different label from that of the other, e.g., the combination of a fluorescent label and a radiolabel. The number of particles of each type present in the sample may be estimated by comparing the results obtained against standard curves prepared in the laboratory. Thus, by measuring the frequency of each label in a given sample, it is possible to identify a particular batch.

(9) The particles may be formed of a material having a different thermal conductivity to the liquid being marked, such that they emit different amounts of heat compared to the surrounding liquid. Such particles can be visualised using infrared (IR) image analysis techniques. The additive may contain two (or more) types of particles having widely different thermal conductivities. Qualitative differences in the heat emitted by the particles will distinguish the respective particle populations. The distribution of the particle types may be selected such that it is possible, by examining the frequency of each particle in a given sample, to identify a particular batch of liquid.

(10) Microscopic analysis of a liquid sample suspected of containing particles can be conducted using any of the well known techniques of microscopy, including light microscopy, phase-contrast microscopy, electron microscopy etc. Phase contrast microscopy, well known from the field of bacteriology generally provides better visualisation of non-labelled particles.

The aforedescribed signal means are primarily intended as a "YES/NO" test, i.e., to indicate the presence of absence of particles in a liquid, although by using a mixed population of particles, it is possible to introduce a degree of specificity into the protocol. However, to provide a test to indicate the origin of a particular sample, e.g., to allow the authorities to identify the party responsible for an oil spillage, it is preferred to provide the particles with a unique marker, typically a macromolecule, such as a nucleic acid or polypeptide, preferably the former to take advantage of PCR technology.

The second (unique) marker may be present on the same particles as that of that of the non-specific marker or on different particles which may or may not have the same size and/or shape of the other particles.

The tagging of substances with nucleic acid is known and disclosed in, e.g., International Patent Publication Nos. WO87/06383 and WO90/14441 and our own copending International Patent Publication No. WO91/17265 (hereby incorporated by reference). The tagging of substances with polypeptides and proteins is also known and disclosed in, e.g., U.S. Pat. Nos. 4,359,363 and 4,441,943. In the former case, the nucleotide base sequence is used to provide a means to encode information, whereas in the latter, it is the sequence of amino acids which to encodes the information.

Nucleic acids can provide a limitless amount of information, because of the variable sequence of bases (adenine, cytosine, guanine and thymine [uracil in the case of RNA which replaces thymine]) contained within the molecule. Probability terms can be calculated for the frequency of a given sequence of bases and, so long as sufficient bases are used, i.e., a sufficiently large DNA molecule is employed as the taggant, then for all practical purposes a unique microtrace can be defined. By using combinations of universal sequences (accepted as industrial standards) and by varying levels of specific sequences, it is possible to identity the type of generic product, the product's origin (company specific sequences), the lot or batch, and even provide an identifier for a unit of commerce.

Both naturally occurring and synthetic nucleic acids are suitable for use as the taggant. They can be single or double stranded. The term "naturally occurring" refers to DNA (or RNA) molecules occurring in nature. An example of naturally occurring DNA molecule is pBR322 which a known sequence has been determined (by D... quencing procedures). The term "synthetic" is applied to DNA (or RNA) synthesized in the laboratory using routine synthesis procedures well known in the relevant art.

Synthetic DNA may be formed from the five naturally occurring bases: adenine, thymine, guanine, cytosine and uracil, and non-naturally occurring bases, e.g., inosine bases, and derivatized nucleotides, such as 7-deazo-2'deoxyguanosine, alkylphosphonate oligodeoxynucleotides, phosphorothioate oligodeoxynucleotides and α-anomeric oligodeoxynucleotides. In certain circumstances, taggants incorporating non-naturally occurring bases may have advantages over those containing only naturally occurring bases, e.g., in stability etc, because they are less likely to be degraded by nuclease activity, by chemically active substances or by environmental conditions, such as heat or ultraviolet radiation. The use of taggants incorporating non-naturally occurring bases is limited only by their ability to be effectively detected by the selected detection means. For tagging methods using the preferred PCR technology, the taggant must be capable of forming duplexes with PCR primers and function as a template for the polymerases used in the PCR procedure.

The preferred molecular structure of the nucleic acid taggant will vary with the means used to detect the nucleic acid. Typically at least 20 nucleotide bases are necessary to ensure adequate specificity for any taggant so that accidental contamination will not lead to false results. The longer the sequence, the higher the potential information content of the taggant, but the more likely that degradation will become a problem. Typically, fragments under 1 kilobase are preferred.

Because of the limits of sensitivity for the detection of nucleic acid, there is an obvious advantage to using methods for amplifying the recovered taggant, such as the PCR procedure disclosed in U.S. Pat. Nos. 4,683,202 and 4,683,195 and European Patent Publication Nos. 258017 and 237362. The PCR method can be used to amplify both single and double stranded DNA taggants, as well as RNA taggants, and allows for the use of extremely low amounts of taggant, typically of the order $1\times10^{-11}$ to $1\times10^{-6}$ g per ml of liquid.

PCR amplification can be carried out in a variety of ways, e.g., inverse and asymmetric PCR are well known variations of the technique. In another variation, promoters for RNA transcription can be incorporated into primers, which, when extended and replicated by PCR, can then be used to create RNA copies of the target sequence. These RNA copies can, in turn, be reverse transcribed into DNA, which can then be amplified by PCR. As with all PCR processes, reaction cycles can be repeated as often as desired.

A double stranded taggant is preferred for PCR amplification, although a single stranded taggant will become double stranded after the first cycle of amplification, because it is less susceptible to degradation, e.g., by nuclease activity. The taggant preferably has a minimum length of about 50 to 70 bases. This permits the hybridization of two primers which are typically about each 20 bases in length, and which, when hybridized to the taggant, are separated by an internal region having a length of from 10 to 30 bases. This internal region is the variable region responsible for giving each taggant its own unique characteristic signal. If this region is 10 bases long, then with the four bases available for DNA/RNA, approximately $1.048\times10^6$ unique taggants can be synthesized. If this region were to be 30 bases in length, approximately $1.15\times10^{18}$ unique taggants can be synthesized.

An outline taggant is as follows:

1. The taggant DNA could be a synthetic, double stranded DNA sequence of 70 to 90 base pairs (bp).

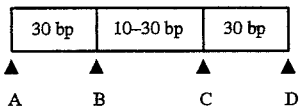

| 30 bp | 10–30 bp | 30 bp |

A     B     C     D

2. The regions AB and CD will be constant for all taggants and will carry pre-determined sequences which recognise appropriate complementary primers for use:
   (i) in PCR amplification and,
   (ii) in DNA sequencing of PCR amplified DNA.
3. The region BC is the variable region of the microtrace DNA responsible for its unique, characteristic signal.
4. One or both ends of the taggant may be labelled with biotin to allow the taggant to be coupled to particles, e.g., microbeads, coated with streptavidin.

The sequence of a preferred taggant is as follows:
(5') GGC CTA GAA GAA GGT TGA AGC TCC GGG GTA ACG CCA GGG TTT TAC AGT GGT GTT GCC CAA GCC TCC AGC AGC TGT GTA TGC CCA TCT CAT CCA ACC TCT T(3') (SEQ ID NO:1)

Bases 1–25 from 5' end of SEQ ID NO:1 (i.e. GGC CTA GAA GAA GGT TGA AGC TCC G) are from primer G-18 sold by Oligo's Etc. Inc. This is one of the primers to be used in PCR amplification.

Bases 26–43 (i.e. GG GTA ACG CCA GGG TTT T) from the 5' end of SEQ ID NO:1 are sequencing primer S-27 from Oligo's Etc. Inc. This is the sequence to be used in sequencing the random piece of the oligonucleotide.

Bases 44–75 (i.e. AC AGT GGT GTT GCC CAA GCC TCC AGC AGC TGT) are a slightly modified sequence chosen at random from the STS gene described in Ballabio et al Nature 393 220 (1990). This is the random sequence which gives a unique label with calculable probabilities of only being this sequence. Modifications are possible, e.g., position 50 is G instead of C; position 56 is C instead of G; and position 75 is T instead of G.

Bases 76–100 from the 5' end SEQ ID NO:1 are from the complement of the primer G-19 sold by Oligo's Etc. Inc. This is the second primer which enables the complementary strand to be amplified by PCR.

Biotin CPG attached to 3' end, during the synthesis of the oligonucleotide, and this gives the anchoring point for the oligonucleotide to attach to the streptavidin or neutralite coated particles.

When detecting nucleic acid by PCR, prior knowledge of the sequence of the taggant is necessary to provide appropriate primers. This knowledge offers a valuable degree of security for those who desire it, for without the primers, which can remain proprietary, the taggant are virtually undetectable.

For detection of taggants, one can use standard nucleic acid hybridization assays or nucleic acid sequencing. Standard nucleic acid hybridization assays include single phase and mixed phase assays, such as sandwich assays, and require prior knowledge of the sequence being detected to provide the appropriate complementary polynucleotides for capture or signal purposes.

Alternatively, the nucleic acid recovered from the samples can be sequenced using conventional sequencing technology. Commercially available kits are suitable for this purpose. The basic sequencing technology is derived from seminal references, such as the Maxam and Gilbert procedure for DNA sequencing described in *Methods in Enzymology*, Vol. 65, pp. 497 to 559. Sequencing is a more difficult procedure, but offers greater reliability than nucleic acid hybridization assays. This is due to the possibility of contamination by extraneous nucleic acid with sufficient complementarity to hybridize to the selected probes and offer false positives.

Based on the outline taggant described above, the following discussion is directed to the particular problems associated with marking hydrophobic liquids, such as oil and other hydrocarbons, using particles having, in addition to the aforedescribed signal means (either on the same or different particles) a unique DNA taggant. The particles preferably comprise a fluorescent label to enable their detection and/or isolation using a fluorescence microscope or flow cytometer.

Because of the hydrophobic nature of the liquid, the particles should be formed of a material which can be stably dispersed in the liquid, without partitioning into the aqueous phase, and which is inert, i.e., non-reactive, for that liquid. Especially preferred are beads formed from polyacrylates, such as poly(acrylic acid) and poly(methacrylic acid).

The beads preferably have an average diameter no greater than 5 μm, with a typical size of between 0.1 to 1 μm. The density of the beads is preferably matched with the specific gravity of the oil, in order to prevent sedimentation or precipitation (creaming) and uneven distribution of the label.

DNA can be attached to the chosen hydrophobic beads in a number of ways. Beads such as paramagnetic carboxyl-modified polystyrene beads (Polysciences, Northampton UK) or paramagnetic tosyl-activated polystyrene beads (Dynal (U.K.) Ltd.), may also be used in this context. The DNA can be attached covalently by linking the 5' terminal free amino group to a suitable target, e.g., the carboxyl group of the carboxyl modified polystyrene. Such techniques are routine (Lund et al., *Nucleic Acid Research*, Vol.16, p. 10861, 1980). Following DNA attachment, the labelled beads can be washed in water and air dried. The excess carboxyl groups on the beads which have not been bonded to a taggant molecule, can be 'capped' with octylamine dissolved in an aqueous solvent, such as dimethylformamide, using dicyclohexylcarbodiimide as the cross-linking reagent. Alternatively, the taggant may be labelled with biotin and the beads coated with streptavidin. Excess streptavidin on the beads which has not been bonded to a taggant molecule can be capped with free biotin.

If only a few DNA molecules, but enough for subsequent PCR amplification, sequence analysis and decoding, are added and bonded to the beads, the proportion of hydrophilic surface (due to the DNA) compared with the overall hydrophobic surface (due to the composition of the bead) is normally insufficient to cause the DNA-bead complex to partition into the aqueous phase. The beads remain in the hydrocarbon until some procedure is used to remove the bead with its attached taggant from the hydrocarbon.

The beads with taggant can be dissolved in solvents, such as chloroform, ether, petroleum ether or toluene, which, in turn, can be dissolved in the oil to be labelled, ensuring an even distribution of the beads and hence the taggant in the oil. The beads can be separated for evaluation of the label by using magnets to pull the beads into one region from which they can be physically separated, or more simply by centrifugation.

To ensure that the beads with attached DNA cannot be removed from the hydrocarbon by aqueous washing, the negative charges associated with the phosphodiester structures of the DNA molecule can be removed by methylation of these groups. Methylation of a region of the DNA molecule will ensure that this part of the molecule becomes hydrophobic, thereby ensuring that the DNA molecule remains within the hydrocarbon phase and is not transferred to the aqueous phase. This can be achieved even if part of the DNA molecule retains its negative charge, i.e., is non-methylated. Methylation of the DNA molecule can be achieved by synthesis with nucleosides synthesized with methyl phosphonates.

Any procedure which favours solubilisation of DNA molecules in hydrocarbons instead of an aqueous phase could be used as an alternative to methylation, e.g., by labelling the nucleoside bases of the DNA with biotin or a hydrophobic hapten, such as fluorescein, dinitrophenol or tri-iodothyronine. Alternatively, sulphonucleotides containing thiophosphates could be incorporated into the taggant and subsequently derivatised with thiol-specific modifying agents, such as iodoethanol.

"MPC-1", "MPC-6", "MPC-E", "DYNABEADS", "DYNASPHERES" and "DETACHaBEAD" are all registered trademarks of DYNAL AS of Oslo, Norway.

We claim:

1. A method of marking a liquid and subsequently detecting that the liquid has been marked and identifying the liquid, which method comprises:

adding to the liquid an additive comprising a plurality of particles in an amount no greater than 1 part weight of particles per $10^6$ parts weight liquid, said plurality of particles comprising signal means to aid their detection, and coding means to aid identification of the liquid, said particles not being visible in the liquid to the naked eye; said additive comprising either (a) two or more particles, each particle having a different signal means, and at least one particle having a code means or (b) a particle having two or more different signal means and at least one code means; one of said signal means being a non-nucleic acid signal means, and another of said signal means being a nucleic acid signal means;

sampling a portion of the liquid containing said additive;

detecting the presence in the liquid sample of said particles having said non-nucleic acid signal means;

detecting the presence of said nucleic acid signal means on particles from the liquid sample; and decoding said code means, thereby detecting that the liquid had been marked and identifying the liquid sample.

2. A method as claimed in claim 1 in which the particles are present in the liquid in an amount no greater than 1 part weight of particles per $10^{10}$ parts weight liquid and the particles have an average size no greater than 1 μm.

3. A method as claimed in claim 2 in which the particles are present in the liquid in an amount of from about 1 part weight of particles per $10^{11}$ parts weight liquid to about 1 part weight particles per $10^{12}$ parts weight liquid and the particles have an average size of from 0.05 to 1 μm.

4. A method as claimed in claim 3 in which about 10 particles are present per ml of liquid.

5. A method as claimed in claim 1 in which the particles comprise microbeads or microspheres.

6. A method as claimed in claim 1 in which said other signal means is a radiolabel and detection of the particles comprises the use of a Geiger-Müller tube, a scintillation counter or the fogging of a photographic film.

7. A method as claimed in claim 1 in which said other signal means is an enzyme and the detection of the particles comprises monitoring the reaction catalysed by the enzyme.

8. A method as claimed in claim 7 in which the enzyme is selected from the group consisting of acetoacetate decarboxylase, alcohol dehydrogenase, aldehyde oxidase, alkaline phosphatase or other lyase, amino acid oxidase, arginine decarboxylase, aspartate decarboxylase, ascorbate oxidase, catalase, galactose oxidase, β-galactosidase, glucose oxidase, glutamate decarboxylase, glycollate oxidase, hexose oxidase, horse radish peroxidase, isomerase, lactic acid dehydrogenase, lactate oxidase, luciferase, lysine decarboxylase, malate oxidase, NADH oxidase, oxalate oxidase, pyruvate decarboxylase, pyruvate oxidase, tryptophan oxidase, urate oxidase and xanthine oxidase.

9. A method as claimed in claims 1 in which said other signal means is a fluorescent, luminescent, phosphorescent or other label capable of producing a photometric signal.

10. A method as claimed in claim 9 in which the fluorescent label is selected from the group consisting of allophycocyanine, phycocyanine, phycoerythrine, bisbenzamide, coumarin, fluorescein or a derivative thereof, rhodamine or other fluorescent dye, ethidium bromide, and propidium iodide; and detection of the particles comprises the use of a fluorescence microscope or a flow cytometer.

11. A method as claimed in claim 1 in which the particles are magnetic and detection of the particles comprises separation and/or concentration of the particles using a magnet.

12. A method as claimed in claim 1 in which the additive comprises particles of two or more different colours or of at least two distinct sizes or shades and the ratio of the differently coloured particles or the differently sized or shaped particles is known.

13. A method as claimed in claim 1 in which the nucleic acid tag is DNA and the detection of the nucleic acid tag comprises the use of polymerase amplification, hybridisation and/or sequencing technology.

14. A method as claimed in claim 1 in which the particles are formed of a naturally occurring or synthetic polymeric resin, a ceramic material or glass.

15. A method as claimed in claim 14 in which the particles are formed from tosyl-activated or carboxyl-modified polystyrene.

16. A method as claimed in claim 1 in which the particles are coated with a first molecule having a binding affinity for a second molecule.

17. A method as claimed in claim 16 in which first molecule is selected from one of the following pairs: an antigen and specific antibody; hormone and hormone receptor; hapten and antihapton; polynucleotide and complementary polynucleotide; polynucleotide and polynucleotide binding protein; biotin and either avidin or strepdavidin; enzyme and enzyme cofactor; and lectin and specific carbohydrate; and the second molecule is the other of said pair.

18. A method as claimed in claim 1 in which the liquid is a hydrocarbon, a paint product, an ink, a perfume, a pharmaceutical, a fertiliser, a herbicide, a pesticide or an organic solvent.

19. A method according to claim 1, wherein said plurality of particles comprises (b) a particle having two or more different signal means and at least one code means.

20. A method according to claim 1, wherein said plurality of particles comprises a type of particle comprising non-nucleic acid signal means, a sequencing primer, an amplification primer and its complementary sequence, a fixed sequence as a nucleic acid signal means, and a variable nucleic acid sequence as a code means for identifying information.

21. A liquid containing an additive comprising a plurality of particles added in an amount no greater than 1 part weight particles per $10^6$ parts weight of liquid, the particles comprising at least two signal means to aid their detection and not being visible in the liquid to the naked eye, the first signal means comprising a nucleic acid and the second said signal means being other than a nucleic acid.

22. A liquid as claimed in claim 21 in which the additive is an additive according to any of claims 1–5, 7, 8, and 10–18.

23. A liquid according to claim 21 in which said additive is according to claim 9.

24. A liquid as claimed in claim 21 which is a hydrocarbon, a paint product, an ink, a perfume, a pharmaceutical, a fertiliser, a herbicide, a pesticide or an organic solvent.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
GGCCTAGAAG  AAGGTTGAAG  CTCCGGGGTA  ACGCCAGGGT  TTTACAGTGG  TGTTGCCCAA    60

GCCTCCAGCA  GCTGTGTATG  CCCATCTCAT  CCAACCTCTT                           100
```